US00PP31861P2

(12) United States Plant Patent
Carruth

(10) Patent No.: US PP31,861 P2
(45) Date of Patent: Jun. 16, 2020

(54) FLORIBUNDA ROSE PLANT NAMED 'WEKJUCISTWE'

(50) Latin Name: *Rosa hybrida*
Varietal Denomination: WEKjucistwe

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 16/350,652

(22) Filed: Dec. 14, 2018

(51) Int. Cl.
*A01H 5/02* (2018.01)
*A01H 6/74* (2018.01)

(52) U.S. Cl.
USPC ..... Plt./143
CPC ..... *A01H 6/749* (2018.05)

(58) Field of Classification Search
USPC ..... Plt./143
CPC ..... A01H 6/749; A01H 5/02
See application file for complete search history.

(56) References Cited

U.S. PATENT DOCUMENTS

| | | | |
|---|---|---|---|
| PP18,473 | P2 | 2/2008 | Carruth |
| PP18,686 | P3 | 4/2008 | Meilland |
| PP23,158 | P2 | 11/2012 | Orard |

OTHER PUBLICATIONS

Help Me Find, 2019.*
Weeks Roses, "All Dressed Up", Wholesale Rose Catalog, 86 pages, 2019.

* cited by examiner

*Primary Examiner* — Keith O. Robinson
(74) *Attorney, Agent, or Firm* — McKee, Voorhees & Sease, PLC

(57) ABSTRACT

A new variety of Floribunda rose plant suitable for garden decoration, having flowers of yellow blushing pink coloration.

1 Drawing Sheet

Classification: The present invention relates to a new *Rosa hybrida* plant.

Variety denomination: The new plant has the varietal denomination 'WEKjucistwe'.

BACKGROUND OF THE INVENTION

This invention relates to a new and distinct variety of Floribunda Rose. It has as its seed parent the variety known as 'WEKvossutono' (U.S. Plant Pat. No. 18,473) and as its pollen parent the variety known as 'ORAfantanov' (U.S. Plant Pat. No. 23,158).

SUMMARY OF THE INVENTION

Among the features which distinguish the new variety from other presently available and commercial rose cultivars known to the inventor are the following combinations of characteristics: its strong fruity to citrus-like fragrance, its elegant old-fashioned flowers of yellow blushing pink coloration and its abundant blooms. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKjucistwe' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'WEKvossutono' by the following combination of characteristics: whereas 'WEKjucistwe' bears very double flowers (about 45 to 65 petals) of yellow blushing pink coloration, 'WEKvossutono' bears very double flowers of butter gold coloration with significantly lesser petalage (about 30 to 45 petals). The new variety has an upright moderately spreading medium height growing habit (about 95 to about 130 cm. in height), whereas the seed parent has a compact and bushy significantly shorter growing habit (about 70 to about 85 cm. in height).

The new variety may be distinguished from its pollen parent, 'ORAfantanov' by the following combination of characteristics: whereas 'WEKjucistwe' bears very double flowers (about 45 to 65 petals) of yellow blushing pink coloration, 'ORAfantanov' bears semi-double flowers of smoky purple magenta blend coloration with significantly lesser petalage (about 13 to 16 petals). The new variety is classified as a Floribunda rose with an upright moderately spreading medium height growing habit (about 95 to about 130 cm. in height), whereas the pollen parent is classified as a Climbing rose with a spreading climbing growing habit with canes about 300 cm. to about 350 cm. in length.

COMPARISON WITH THE CLOSEST COMMERCIALLY AVAILABLE CULTIVAR

The new variety may be distinguished from its closest commercially available cultivar, 'MElpoten' (U.S. Plant Pat. No. 18,686) by the following combination of characteristics: whereas 'WEKjucistwe' bears very double flowers (about 45 to 65 petals) with a strong fruity to citrus-like fragrance, 'MElpoten' bears double flowers with significantly lesser petalage (about 24 to 25 petals) and with no fragrance. The new variety has an upright moderately spreading medium height growing habit (about 95 to about 130 cm. in height), whereas the closest commercially available cultivar has a bushy and semi-erect shorter growing habit (about 90 to about 100 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon the Colour Chart of The Royal Horticultural Society (2001) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety sometimes bears its flowers singly, sometimes in clusters of two to five or more per stem. Flowers may be presented in rounded clusters on strong short to medium length stems (about 14 to about 42 cm.). The cluster ranges from about 10.5 to about 14.0 cm. in diameter. Outdoors, the plant blooms abundantly and nearly continuously during the growing season. The flowers have a strong fruity to citrus-like fragrance.

BUD

The peduncle is about 5 to about 6 cm. in length, of average to heavy caliper (about 0.3 to about 0.4 cm. in diameter), and erect. It is almost entirely smooth, with very few stipitate glands. Peduncle color is near 146D and often heavily suffused, especially on the side exposed to the sun, with between 178A and 183B.

Before the calyx breaks, the bud is about 2.1 to about 2.3 cm. in diameter at the widest point, about 2.6 to about 3.1 cm. in length, and globular in shape. The surface of the bud bears few foliaceous appendages that do not extent beyond ¼ of the tip of the bud. Bud color is between 5B and 5C often heavily suffused, especially on the tip exposed to the sun, with between 53B and 53D.

The sepals are 5 per flower, about 3.0 to about 3.4 cm. in length and about 0.8 to about 0.9 cm. in width at the widest point. The outer surface color of the sepal is between 138A and 138B often heavily suffused, especially on the side exposed to the sun, with between 183A and 183B. The outer surface of the sepal is somewhat smooth with between 0 to 2 foliaceous appendages and with some hairs and glandular bloom. The inner surface color of the sepal is near 138C broadly bordered by near 157D. After the sepals open, the inner surface color is sometimes lightly suffused, especially on the area exposed to the sun, with near 184D. The inner surface of the sepal is covered and edged with fine wooly tomentum; sepal margins are entire and without stipitate glands. The sepals are fugacious, spear-shaped and curled to recurved in shape with acute apices.

The receptacle of the flower is of medium length (about 0.6 to about 0.7 cm.) and of average caliper (about 0.9 to about 1.0 cm. in diameter). The receptacle is funnel shaped in form. Its surface is smooth with thick fleshy walls. The receptacle color is near 138B in color and often suffused with near 184B when exposed to the sun.

As the petals open (after the calyx breaks), the bud is about 3.0 to about 3.2 cm. in diameter at the widest point, about 3.0 to about 3.2 cm. in length, and globular in form. The color of the under surfaces of the newly opened petals is between 4B and 4C. At the point where the petal attaches, there is a small zone of near 4A. The color of the upper surfaces of the newly opened petals is between 4B and 4C. At the point where the petal attaches, there is a small zone of near 4A.

BLOOM

When fully open, the bloom ranges from about 7 to about 9 cm. in diameter. Petalage is very double with about 45 to 65 petals and about 6 to 9 petaloids irregularly arranged. When partially open, the bloom form is cupped, and the petals are somewhat loosely arranged with petal edges somewhat reflexed outward. When fully open, the bloom form is somewhat flat to cupped and the petals are loosely arranged with petal edges somewhat reflexed outward.

PETALS

The substance of the petals is somewhat thin in thickness, with upper surfaces somewhat shiny and smooth and under surfaces somewhat shiny to matte. The petals are about 4.3 to about 5.0 cm. in length and about 3.2 to about 4.0 cm. in width at the widest point. Petal margins are entire.

The outer petals are round to orbicular in shape with rounded apices and sometimes slightly notched with one to two notches.

The inner petals are oval to ovate in shape with rounded apices and sometimes slightly notched with one to two notches.

Petaloids are about 1.5 to about 2.5 cm. in length and about 1.0 to about 2.5 cm. in width at the widest point. Petaloids are shaped somewhat spatulate to oblanceolate with moderately rounded apices.

NEWLY OPENED FLOWER

The under surface color of the outer petals is between 4B and 4C. At the point where the petal attaches, there is a small zone of near 4A. The upper surface color of the outer petals is between 4B and 4D. At the point where the petal attaches, there is a small zone of near 4A. The small zone on the under and upper surface is about 0.4 to about 0.5 cm in width and about 0.3 and 0.4 cm in length.

The under and upper surface color of the intermediate and inner petals is between 4B and 4C.

The under and upper surface colors of the petaloids are similar in coloration to the upper and under surfaces of the intermediate and inner petals.

The general tonality of the newly opened flower is between 4B and 4C.

THREE-DAY-OLD FLOWER

The under and upper surface color of the outer petals is near 4C except on the outer third of the petal. There the color has changed to near N66D. At the point where the petal attaches, there is a small zone of near 4B. The small zone on the under and upper surface is about 0.4 to about 0.5 cm in width and about 0.3 and 0.4 cm in length.

The under surface color of the intermediate and inner petals is near 4B with near N66D on the outer third of the petal. The upper surface color of the intermediate and inner petals is near 4B except on the petal outer third where the color has changed to near N66B.

The under and upper surface colors of the petaloids are similar in coloration to the upper and under surfaces of the intermediate and inner petals.

The general tonality of the three-day-old flower is near 4B with near N66B on the outer edges.

On the spent bloom, the petals usually drop off cleanly.

In November in Wasco, Calif., blooms on the bush growing outdoors generally last about four to five days. Cut roses from plants grown outdoors and kept at normal indoor living temperatures generally last about five days.

MALE REPRODUCTIVE ORGANS

Stamens are average in number (average about 45) and are arranged regularly about the pistils; a few are mixed with petaloids. The filaments are of medium length (about 0.6 to about 0.7 cm.) most with anthers. Filaments are near 6A in color. The anthers are of medium size (about 0.15 to about 0.2 cm in diameter at the widest point) for the class and all open approximately at the same time. Anther color when immature is near 164C on the external part and near 164B on the internal part. Anther color at maturity is near N172D on the external part and near 168C on the internal part. Pollen is abundant and between 175C and 175D in color.

FEMALE REPRODUCTIVE ORGANS

Pistils vary in number (average about 25). The styles are somewhat even, average in length (about 0.5 to about 0.6 cm.), average in caliper (about 0.1 to about 0.15 cm), and bunched together. Stigma color is between 3C and 3D. Style color is between 1B and 1A. Ovaries are generally all enclosed in the calyx. The ovaries are of medium size (about 0.15 to about 0.2 cm in diameter at the widest point) and near 155C in color.

Hips are of moderately short to average length (about 0.9 to about 1.4 cm.), rounded in form with a flat top, and between 31A and 30C in color when ripe. The hip surface is smooth with thick fleshy walls.

The seeds are irregularly rounded, smooth in texture, approximately 8 to about 21 per hip, about 0.4 to about 0.6 cm. in diameter at the widest point and between 164D and 165D in color.

FOLIAGE

The compound leaves are usually comprised of three to seven leaflets and are borne abundantly. The five-leaflet leaves are about 13 to about 15 cm. in length and about 8 to about 10 cm. in width at the widest point, leathery in texture on both sides, and somewhat glossy in finish on the upper side and matte in finish on the under side. The leaves have a pinnate venation pattern. The terminal leaflets are about 5.0 to about 5.5 cm. in length and about 3.5 to about 4.0 cm. in width at the widest point, shaped ovate with acute to acuminate apices and somewhat rounded bases. Their margins are simply serrate.

The upper surface color of the mature leaf is between 137A and 147B. The under surface color of the mature leaf is near 147B. The under and upper colors of the leaf veins on the mature leaf are similar in coloration to the upper and under surfaces colors of the mature leaf The upper surface color of the young leaf is between 147A and 147B, sometimes suffused with between 178B and 178C. The under surface color of the young leaf is near 147B, sometimes suffused with between 147A to 147B. The under and upper colors of the leaf veins on the young leaf are similar in coloration to the upper and under surfaces colors of the young leaf.

The rachis is about 8.0 to about 10 cm. in length, about 0.15 to about 0.16 cm in width at the widest point, and somewhat rough. The upper side is moderately grooved with very few hairs and stipitate glands on the edges of the grooves. The under side of the rachis is somewhat rough with few hairs and stipitate glands and few small prickles. The rachis color is near 146D on the under side and near 146B on the upper side, sometimes suffused on the young leaves with near 178B.

The stipules are about 1.3 to about 1.4 cm. in length and of medium width (about 0.4 to about 0.5 cm.) with somewhat short to medium length (about 0.3 to about 0.5 cm) straight points that usually turn out at an angle of more than 90 degrees and sometimes recurve toward the stem. The under and upper surface color of the stipule is between 146C and 146D sometimes suffused with between 178B to 178C. The upper and under surfaces of the stipules are smooth in texture.

The petiole is average in caliper (about 0.15 to about 0.16 cm) and smooth. The upper side is moderately grooved with few hairs and stipulate glands on the edges of the grooves. The under side of the petiole is smooth with few hairs and stipulate glands. Petiole color is near 146D on the under side and near 146B on the upper side, sometimes suffused on the young leaves with near 178B.

The plant displays an average degree of resistance to powdery mildew (*Sphaerotheca pannosa*), downy mildew (*Peronospora sparsa*) and rust (*Phragmidium* sp.) as compared to other commercial varieties grown under comparable conditions in Wasco, Calif. The planes winter hardiness and drought/heat tolerance are yet to be determined.

GROWTH

The plant has an upright moderately spreading medium height growing habit (about 95 to about 130 cm. in height and about 110 to about 130 cm. spread at the widest point), with full branching. It displays vigorous growth and the canes are of medium caliper for the class (about 1.5 to about 2.6 cm. in diameter at the widest point).

The color of the major stems is between 146B and 146C. The major stems are rough in texture and they bear several large prickles that are about 0.7 to about 0.9 cm. in length. The large prickles are hooked moderately downward with medium length (about 0.5 to about 0.8 cm) to a broad slightly rounded base; prickle color is near 176B. The major stem bears very few small prickles of similar color and shape to the large prickles.

The color of the branches is near 146C and have on the youngest growth, especially where exposed to the sun, 178B as an overlay. The branches are rough in texture and they bear several large prickles which are of similar size and shape to the large prickles on the major stems; prickle color is between 183C and 183D. The branches bear very few small prickles of similar shape and coloration.

The color of the new shoots is between 183C and 183D which quite quickly become 146C as the shoot matures. The new shoots are rough in texture and they bear many large prickles which are of similar size and shape to the large prickles on the major stems; prickle color is near 183C. The shoots bear very few small prickles of similar shape and coloration.

I claim:

1. A new and distinct Floribunda rose plant substantially as described and illustrated herein.

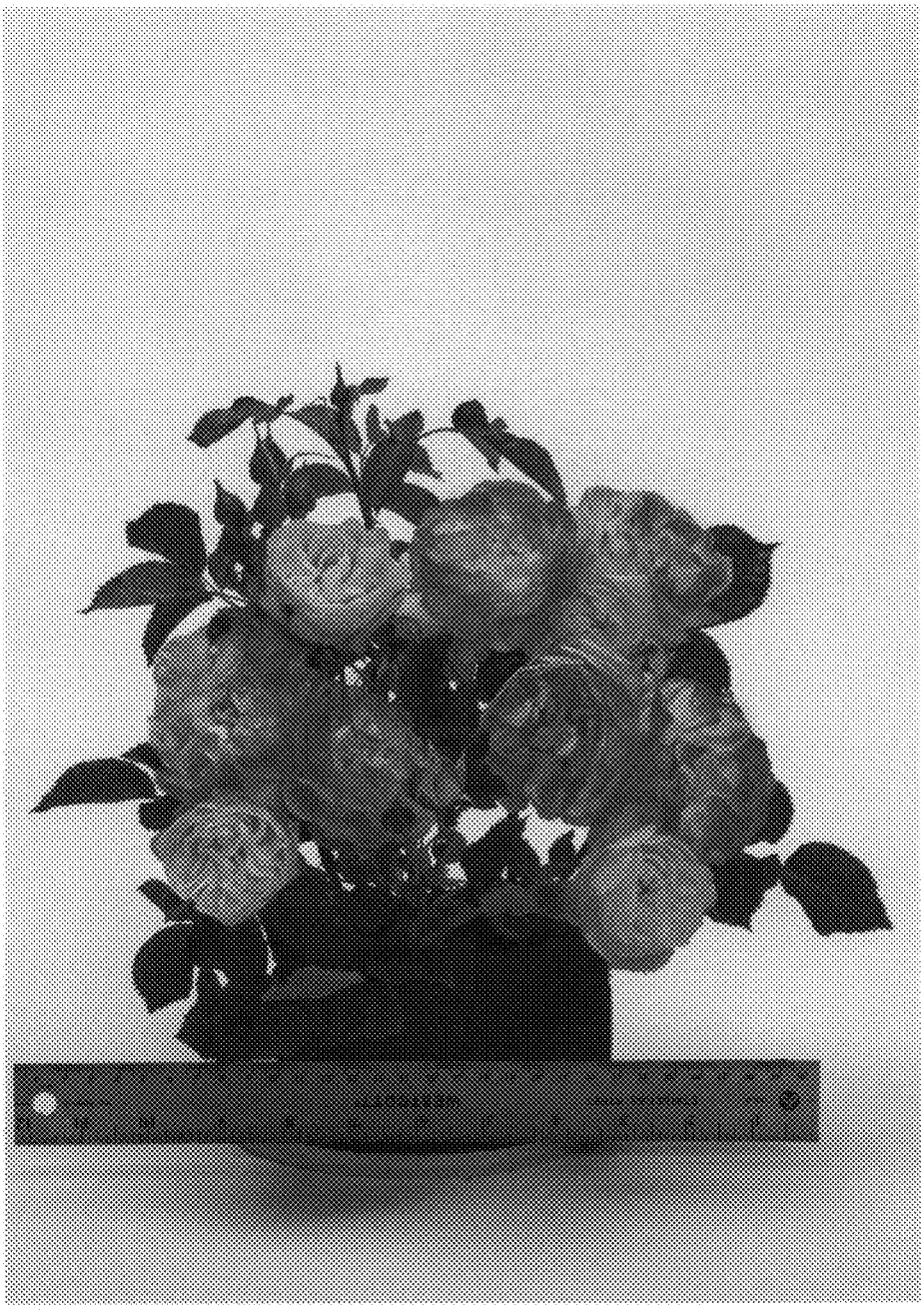

* * * * *